(12) United States Patent
Chono et al.

(10) Patent No.: US 8,420,117 B2
(45) Date of Patent: Apr. 16, 2013

(54) PATCH FORMULATION FOR EXTERNAL USE

(75) Inventors: Hideharu Chono, Tsukuba (JP); Toshiro Yamaguchi, Tsukuba (JP); Hisakazu Kurita, Tsukuba (JP); Tetsuro Tateishi, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 12/831,190

(22) Filed: Jul. 6, 2010

(65) Prior Publication Data

US 2011/0027365 A1    Feb. 3, 2011

Related U.S. Application Data

(63) Continuation of application No. 10/754,592, filed on Jan. 12, 2004, which is a continuation of application No. 10/031,747, filed as application No. PCT/JP00/04945 on Jul. 25, 2000, now abandoned.

(30) Foreign Application Priority Data

Jul. 27, 1999    (JP) .................................... 11/212921

(51) Int. Cl.
*A61K 9/70*    (2006.01)
*A61K 9/14*    (2006.01)
*A61K 31/24*   (2006.01)
*A61L 15/00*   (2006.01)
*A61L 15/16*   (2006.01)

(52) U.S. Cl.
USPC .......... 424/449; 424/443; 424/445; 424/446; 424/447; 424/448; 424/484; 514/534; 514/552; 514/724

(58) Field of Classification Search .................. None
See application file for complete search history.

*Primary Examiner* — Robert A Wax
*Assistant Examiner* — Jeffrey T Palenik
(74) *Attorney, Agent, or Firm* — Sughrue Mion, PLLC

(57) ABSTRACT

A patch formulation for external use where a basic drug, an organic acid and an organic acid salt are combined as essential components is disclosed. The basic drug is preferably in the form of its acid addition salt. The organic acid is preferably a carboxylic acid having carbon atoms of 2 to 7, and more preferably at least one acid selected from the group consisting of acetic, lactic, tartaric, citric, malic, benzoic and salicylic acids. The organic acid salt is preferably a metal salt of a carboxylic acid, and more preferably sodium acetate.

3 Claims, No Drawings

PATCH FORMULATION FOR EXTERNAL USE

This application is a continuation of application Ser. No. 10/754,592, filed Jan. 12, 2004 (now abandoned), which is a continuation of application Ser. No. 10/031,747, filed Jan. 24, 2002 (now abandoned), which is a National Stage Entry of PCT/JP00/04945, filed Jul. 25, 2000, which claims priority to Japanese Patent Application No. 11/212921, filed Jul. 27, 1999.

TECHNICAL FIELD

The present invention relates to a patch formulation for external use. In particular, the invention relates to a patch formulation for external use comprising a basic drug, an organic acid and an organic acid salt, having a good percutaneous absorption property and good stability.

BACKGROUND ART

Conventionally, various methods for administrating drug have been known such as oral, rectal, intracutaneous or intravenous administration, and among them oral administration is employed most widely. However, oral administration has some defaults, for example, that a drug is prone to a first pass effect in the liver, and that the blood level of a drug becomes transiently higher than that required after it is administered orally. In addition, such adverse reactions as gastrointestinal disturbance, nausea, anorexia and so on have been often reported after oral administration. Furthermore, considering an increase in the number of patients with difficulty in deglutition in this aged society, pharmaceutical formulations easier to take are required clinically. Therefore, patch formulations for external use have been actively developed and such products are also marketed, because they can eliminate these defaults of oral administration and can be taken more safely and more continually by patients as pharmaceutical formulation easy to take.

But, many drugs have so low percutaneous absorption that their patch formulations for external use are difficult to develop, thus hindering such formulations from functioning adequately. In other words, normal skin has inherently a barrier function to prevent foreign bodies from intruding into the body, whereby many drugs are not well absorbed percutaneously when a typical base is used for such patch formulations.

It has thus been attempted to elevate percutaneous absorption of drugs through the corneal layer of epidermis, generally by means of addition of a so-called percutaneous absorption enhancer into the base. For example, absorption promoting compositions comprising a lower alkyl amide, such as a combination of dimethyl acetamide with ethyl alcohol, isopropyl alcohol or isopropyl palmitate (U.S. Pat. No. 3,472,931); a combination of 2-pyrrolidone with a suitable oil, or a straight-chain fatty acid with an alcoholic ester (U.S. Pat. No. 4,017, 641); a lower alcohol and an alcohol having carbon atoms of 7 to 20; an aliphatic acid hydrocarbon having carbon atoms of 5 to 30, an alcoholic ester of an aliphatic carboxylic acid having carbon atoms of 19 to 26, a mono- or di-ether having carbon atoms of 10 to 24 or a combination of a ketone having carbon atoms of 11 to 15 (Japanese Patent Laid-Open No. 61-249934) and the like were disclosed. However, these conventional absorption enhancers and absorption promoting compositions are not sufficiently safe to the skin. In addition, in a patch formulation for external use containing a basic drug in the form of an acid addition salt, the drug could hardly be expected to exhibit its effect.

Further, a technique of using a combination of a drug and an organic acid is also described for patch formulations for external use. For example, a tape formulation where betamethasone valerate and an organic acid are combined together with a natural rubber based adhesive (Japanese Patent Laid-Open No. 56-61312), a tape formulation where a non-steroidal anti-inflammatory analgesic and an organic acid are combined together with an acrylic adhesive (Japanese Patent Laid-Open No. 62-126119), also a poultice-type formulation where methyl salicylate as a drug component, an emulsifier, an organic acid, a plasticizer, a tackifying resin and water are combined together with styrene-isoprene-styrene block copolymer (Japanese Patent Laid-Open No. 63-159315) and the like were disclosed. In any of these specifications, however, no organic acid salt is used, and the organic acid is used to improve stability, elevate solubility and adjust pH, but not to elevate percutaneous absorption of the drug. Furthermore, any drug in these specifications is acidic or neutral, and use of the organic acid therein is not intended to elevate either skin permeation or stability of a basic drug through ion pair formation as in the present invention.

Also, another technique is attempted to elevate skin permeation of a basic physiologically active substance. For example, a tape formulation where citric acid and isoproterenol hydrochloride are combined together with an acrylic adhesive (Japanese Patent Laid-Open No. 63-79820), and a tape formulation where an organic acid and vinpocetine are combined together with an acrylic adhesive (Japanese Patent Laid-Open No. 5-25039) were described. However, these formulations have a problem of irritability when detached, and they cannot release a sufficient amount of a drug for therapy.

Also, yet another technique of combining a drug and an organic acid as a percutaneous dosage formulation is disclosed. For example, a formulation containing an organic acid and a glycol together with a salt of a non-steroidal anti-inflammatory analgesic (Japanese Patent Laid-Open No. 62-181226), and a patch formulation comprising an alkaline metal salt of a non-steroidal anti-inflammatory analgesic and an organic acid more acidic than the free form of the non-steroidal anti-inflammatory analgesic (Japanese Patent Publication No. 7-47535) were described. These disclosures, however, do not relate to basic drugs but to acidic drugs. Also disclosed is a formulation where a basic drug or its salt, an alcohol having carbon atoms of 2 to 5, an organic acid having carbon atoms of 2 to 5 and a carboxylic acid ester having carbon atoms of 16 to 20 are combined, although application of an organic acid salt is not described therein.

Yet another technique to formulate a patch formulation is disclosed in WO 96/16642, where an organic acid salt is contained together with the salt form of a basic drug, but it is not disclosed that a combination of an organic acid with an organic acid salt may elevate the skin permeability of the drug, nor the physical stability of the patch formulation for external use, such as adhesiveness or appearance.

Accordingly, no patch formulation for external use has yet been known that contains a basic drug in the form of an acid addition salt, thereby possessing excellent stability and also a desirable percutaneous absorption property of the drug therein.

DISCLOSURE OF THE INVENTION

The objects of the present invention is to dissolve the above mentioned problems of the prior art and to provide a patch formulation for external use comprising a basic drug, which has a good percutaneous absorption property of the drug and good stability.

After many efforts to dissolve the above mentioned problems, the inventors have found that, by including particular amounts of an organic acid and an organic acid salt into a patch formulation for external use which contains a basic drug in the form of an acid addition salt, more stable ion pairs are formed therein than in a patch including the organic acid salt alone, and a quasi-stable state, capable of elevating skin permeability of the drug therein, can be maintained constantly therein, and the finding has resulted in completion of the present invention.

Accordingly, the present invention relates to a patch formulation for external use characterized by that it contains a basic drug, an organic acid and an organic acid salt as essential components.

BEST MODE FOR CARRYING OUT THE INVENTION

The invention will be described in detail below.

A patch formulation for external use according to the present invention preferably comprises a adhesive layer, and further may comprise, for example, a backing layer for supporting the adhesive layer and a release liner established on the adhesive layer. Preferably, the patch formulation according to the present invention comprises a basic drug, an organic acid and an organic acid salt in the adhesive layer.

In the patch formulation according to the present invention, the basic drug used in the adhesive layer is preferably as an acid addition salt of the basic drug. The acid addition salts of the basic drug are not limited in particular, but include, for example, hypnotics/sedatives (for example, flurazepam hydrochloride, rilmazafone hydrochloride), antipyretic antiinflammatory analgesics (for example, butorphanol tartrate, perisoxal citrate), antimigraine agents (for example, ergotamine tartrate, ergotamine mesilate), stimulants/antihypnotics (for example, methamphetamine hydrochloride, methylphenidate hydrochloride), anti-psychoneurotics (for example, chlorpromazine hydrochloride, imipramine hydrochloride), local anesthetics (for example, lidocaine hydrochloride, procaine hydrochloride), agents for urinary organs (for example, oxybutynin hydrochloride), skeletal muscle relaxants (for example, tizanidine hydrochloride, eperizone hydrochloride, pridinol mesilate), agents for autonomous nerves (for example, carpronium chloride, neostigmine bromide), anti-Parkinsonian agents (for example, pergolide mesilate, bromocriptine mesilate, trihexyphenidyl hydrochloride, amantadine hydrochloride), antihistamines (for example, clemastine fumarate, diphenhydraminetannate), bronchodilators (for example, tulobuterol hydrochloride, procaterol hydrochloride), cardiotonics (for example, isoprenaline hydrochloride, dopamine hydrochloride), coronary vasodilators (for example, diltiazem hydrochloride, verapamil hydrochloride), peripheral vasodilators (for example, nicametate citrate, tolazoline hydrochloride), agents for circulatory organs (for example, flunarizine hydrochloride, nicardipine hydrochloride, benidipine hydrochloride, efonidipine hydrochloride, bisoprolol fumarate, timolol maleate, diltiazem hydrochloride, metoprolol tartrate), antiarrhythmics (for example, propranolol hydrochloride, alprenolol hydrochloride), antiallergics (for example, ketotifen fumarate, azelastine hydrochloride), antidizzying agents (for example, betahistine mesilate, diphenidol hydrochloride), anti-serotonin-receptor antiemetics (for example, ondansetron hydrochloride, granisetron hydrochloride) and narcotic analgesics (for example, morphine hydrochloride, fentanyl citrate).

These basic drugs may be used alone or in combination, and in either form of inorganic or organic salts. The basic drug may be added preferably in the range from 0.1 to 20% by weight of the total weight of the composition of the adhesive layer, considering sufficient skin permeation as a patch formulation and the effect on the adhesive property. Addition of less than 0.1% by weight of the drug results in an insufficient potency, while addition of more than 20% by weight results in a poor physical property as a patch formulation.

In the patch formulation for external use according to the present invention, the organic acid used in the adhesive layer is not limited in particular, but preferably a carboxylic acid having carbon atoms of 2 to 7. Such organic acids having carbon atoms of 2 to 7 include aliphatic mono-, di- or tri-carboxylic acids (for example, acetic, propionic, isobutyric, lactic, maleic, fumaric, pyruvic, oxalic, succinic and tartaric acids), and aromatic carboxylic acids (for example, salicylic and benzoic acids). In particular, acetic, lactic, tartaric, citric, malic, benzoic and salicylic acids are preferable among these.

These organic acids may be used alone or in combination. These organic acids may be added preferably in the range from 0.01 to 20% by weight of the total weight of the composition of the adhesive layer, more preferably from 0.1 to 15% by weight, most preferably from 0.1 to 10% by weight, considering stability and skin irritation of the patch formulation. Addition of less than 0.01% by weight of the organic acid into the adhesive layer results in poor stability, while addition of more than 20% by weight results in skin irritation.

The ratio of the acid addition salt of the basic drug to the organic acid, when they are compounded, preferably ranges from 5:1 to 1:5 (by equivalent ratio). If the ratio of the acid addition salt of the basic drug to the organic acid is out of the range from 5:1 to 1:5, both stability and skin permeability will be reduced.

In the patch formulation for external use according to the present invention, the organic acid salt used in the adhesive layer is not limited in particular, but respective water soluble inorganic salts of aliphatic mono-, di- or tri-carboxylic acids (for example, acetic, propionic, isobutyric, caproic, caprylic, lactic, maleic, pyruvic, oxalic, succinic and tartaric acids), aromatic carboxylic acids (for example, phthalic, salicylic, benzoic and acetyl salicylic acids), alkyl sulfonic acids (for example, ethane sulfonic acid, propyl sulfonic acid, butane sulfonic acid and polyoxyethylene alkyl ether sulfonic acid), alkyl sulfonic acid derivatives (for example, N-2-hydroxyethylpiperidine-N'-2-ethane sulfonic acid (abbreviated as HEPES below)) and cholic acid derivatives (for example, dehydrocholic acid), may be exemplified. Among these, metal carboxylates are preferable, and sodium acetate is especially preferable. Although these organic acid salts may be dehydrated or hydrated, they are preferably a dehydrate when they are used in a hydrophobic adhesive layer.

These organic acid salts may be used alone or in combination. These organic acid salts may be added preferably in a range from 0.01 to 20% by weight of the total weight of the composition of the adhesive layer, more preferably from 0.1 to 15% by weight, most preferably from 0.1 to 10% by weight, considering skin permeability and skin irritation of the patch formulation. Addition of less than 0.01% by weight of the organic acid salt results in poor skin permeability, while addition of more than 20% by weight results in skin irritation.

The ratio of the acid addition salt of the basic drug to the organic acid salt, preferably ranges from 5:1 to 1:5 (by equivalent ratio). If the ratio of the acid addition salt of the basic drug to the organic acid salt is out of the range from 5:1 to 1:5, both skin permeability and physical property will deteriorate.

Furthermore, the ratio of the organic acid to the organic acid salt, preferably ranges from 3:1 to 1:20 (by equivalent ratio), more preferably from 2:1 to 1:15 (by equivalent ratio), and most preferably from 1:1 to 1:10 (by equivalent ratio). If the ratio of the organic acid to the organic acid salt is out of the range from 3:1 to 1:20, both skin permeability and stability will be decreased.

In the patch formulation for external use according to the present invention, the adhesive layer may contain not only the basic drug, the organic acid and the organic acid salt as essential components described above, but also an absorption enhancer, a plasticizer, a lipophilic/hydrophobic polymer, a tackifying resin and other additives, if required.

Any compound that is known to promote the absorption of a drug by the skin may be suitable as absorption enhancer, such as a fatty acid, an aliphatic alcohol, a fatty acid ester or ether, each having carbon atoms of 6 to 20; an aromatic organic acid, an aromatic alcohol, an aromatic organic acid ester or ether (the above compounds may be saturated or unsaturated, and cyclic, linear or branched); in addition, a lactate ester, an acetate ester, a monoterpene-type compound, a sesquiterpene-type compound, Azone, an Azone derivative, a glycerol fatty acid ester, a sorbitan fatty acid ester (Span type), a polysorbate (Tween type), a polyethylene glycol fatty acid ester, a polyoxyethylene-hardened castor oil (HCO type) or a sucrose fatty acid ester.

Preferable examples of the above described absorption enhancer are caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methyl laurate, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, ethyl acetate, propyl acetate, geraniol, thymol, eugenol, terpineol, l-menthol, borneol, d-limonene, isoeugenol, isoborneol, nerol, dl-camphor, glycerol mono-laurate, glycerol mono-oleate, sorbitan mono-laurate, sucrose monolaurate, polysorbate 20, propylene glycol, polyethylene glycol mono-laurate, polyethylene glycol mono-stearate, HCO-60, pyrothiodecane and others, and especially preferable examples are lauryl alcohol, l-menthol, propylene glycol and pyrrothiodecane.

These absorption enhancers may be used alone or in combination. These absorption enhancers may be added preferably in the range from 0.01 to 20% by weight of the total weight of the composition of the adhesive layer, more preferably from 0.05 to 10% by weight, most preferably from 0.1 to 5% by weight, considering skin permeability and skin irritation, such as erythema or edema, of the patch formulation.

In the patch formulation for external use according to the present invention, the plasticizer used in the adhesive layer is a petroleum-based oil (for example, paraffinic process oil, naphthenic process oil or aromatic process oil), squalane, squalene, a vegetable oil (for example, olive oil, camellia oil, castor oil, tolu oil or peanut oil), silicone oil, a dibasic acid ester (for example, dibutyl phthalate or dioctyl phthalate), a liquid rubber (for example, polybutene or liquid isoprene rubber), diethylene glycol, polyethylene glycol, glycol salicylate, propylene glycol, dipropylene glycol, triacetin, triethyl citrate, crotamiton or diethyl sebacate. Among these, liquid paraffin, liquid polybutene, glycol salicylate and crotamiton are especially preferable.

These plasticizers may be used alone or in combination. These plasticizers may be added in total preferably in the range from 10 to 70% by weight of the total weight of the composition of the adhesive layer, more preferably from 10 to 60% by weight, most preferably from 10 to 50% by weight, so as to have good skin permeability and maintain good cohesion as a patch formulation.

In the patch formulation for external use according to the present invention, the lipophilic/hydrophobic polymer used in the adhesive layer is styrene-isoprene-styrene block copolymer (abbreviated as "SIS" below), isoprene rubber, polyisobutylene (abbreviated as "PIB" below), styrene-butadiene-styrene block copolymer (abbreviated as "SBS" below), styrene-butadien rubber (abbreviated as "SBR" below) or an acrylic polymer (a copolymer of at least two monomers selected from the group consisting of 2-ethylhexyl acrylate, vinyl acetate, methacrylates, methoxyethyl acrylate and acrylic acid). Among these, SIS, PIB, blends of SIS and PIB, and acrylic polymers are especially preferable.

These hydrophobic polymers may be used alone or in combination. A hydrophobic polymer such as SIS, PIB or the like may be added preferably in the range from 10 to 60% by weight by weight of the total weight of the composition of the adhesive layer, more preferably from 15 to 50% by weight, and most preferably from 18 to 40% by weight, so as to form the adhesive layer and have good skin permeability as a patch formulation. An acrylic polymer may be added preferably in the range from 10 to 98% by weight, more preferably from 20 to 98% by weight, and most preferably from 30 to 98% by weight on the same basis.

In the patch formulation for external use according to the present invention, the tackifying resin used in the adhesive layer is a rosin derivative (for example, rosin, rosin glycerol ester, hydrogenated rosin, hydrogenated rosin glycerol ester or pentaerythritol rosin ester), alicyclic saturated hydrocarbon resin, aliphatic hydrocarbon resin, terpene resin or maleate resin. Among these, hydrogenated rosin glycerol ester, alicyclic saturated hydrocarbon resin, aliphatic hydrocarbon resin and terpene resin are especially preferable.

These tackifying resins may be used alone or in combination. These tackifying resins may be added preferably in the range from 10 to 70% by weight of the total weight of the composition of the adhesive layer, more preferably from 15 to 60% by weight, and most preferably from 20 to 50% by weight, considering adhesive strength and skin irritation upon detachment of the patch, formulation.

In the patch formulation for external use according to the present invention, the adhesive layer may contain additives such as antioxidant, filler, crosslinker, preservative and UV absorber, if required.

Examples of antioxidants include tocopherols and ester derivatives thereof, ascorbic acid, stearoyl ascorbate, nordihydroguaiaretic acid, dibutyl-hydroxytoluene (BHT) and butyl-hydroxyanisole.

Examples of fillers include calcium carbonate, magnesium carbonate, silicates (for example, aluminum silicate and magnesium silicate), silicic acid, barium sulfate, calcium sulfate, calcium zincate, zinc oxide and titanium dioxide.

Examples of crosslinkers include thermoset resin, such as amino resin, phenol resin, epoxy resin, alkyd resin and unsaturated polyester, isocyanate compounds, blocked isocyanate compounds, organic crosslinkers and inorganic crosslinkers, such as metals or metallic compounds.

Examples of preservatives include ethyl p-hydroxybenzoate, propyl p-hydroxybenzoate and butyl p-hydroxybenzoate.

Examples of UV absorbers include p-aminobenzoic acid derivatives, anthranilic acid derivatives, salicylic acid derivatives, coumarin derivatives, compounds based on amino acids, imidazoline derivatives, pyrimidine derivatives and dioxane derivatives.

In the patch formulation for external use according to the present invention, these additives, such as antioxidant, filler, crosslinker, preservative and UV absorber, may be added preferably at 10% by weight or less in total of the total weight of the composition of the adhesive layer, more preferably at 5% by weight or less, and most preferably at 2% by weight or less.

A process of producing a patch formulation according to the present invention, having a composition described above and for external use, may not be limited but any applicable one. As an example, of ter thermally melting a matrix composition containing a drug and then coating it on a piece of release paper or a substrate, the coating can be attached to the substrate or a piece of the release paper in order to prepare the patch formulation. In addition, after dissolving the matrix composition containing the drug in a solvent, such as toluene, hexane or ethyl acetate, then casting the solution on a piece of the release paper or the substrate, and further drying the coating by solvent evaporation, the coating can be attached to the substrate or a piece of the release paper in order to prepare the patch formulation.

The patch formulation for external use according to the present invention is preferably a non-water soluble system, containing no water.

Further, provided that the patch formulation for external use according to the present invention comprises a basic drug, an organic acid salt and an organic acid, the other composition or the material of any other component may be of any type or any kind.

The backing layer, which can be established to support the adhesive layer, can be formed from an elastic or non-elastic substrate. The substrate can be selected from, for example, cloth, unwoven cloth, polyurethane, polyester, polyvinyl acetate, polyvinylidene chloride, polyethylene, polyethylene terephthalate, aluminum sheet and composite materials thereof.

The release liner, which can be established on the adhesive layer, can be formed by using film made of, for example, polyethylene terephthalate, polyester, polyvinyl chloride or polyvinylidene chloride, or laminated film of quality paper or the like with polyolefin, each film being siliconized on the side contacting the adhesive layer.

EXAMPLES

The present invention will be described in more detail by means of the following examples. In the Examples, Comparative Examples and Test Examples, "%" is always intended to mean "% by weight".

Example 1

| | |
|---|---|
| Sodium acetate | 1.0% |
| Tartaric acid | 0.5% |
| Acrylic adhesive polymer | 93.5% |
| (PE-300: Nippon Carbide Industries) | |
| Isocyanate crosslinker | 1.0% |
| (CK-100: Nippon Carbide Industries) | |
| Pyrothiodecane | 2.0% |
| Tizanidine hydrochloride | 2.0% |
| Total | 100.0% |

From among these components, tartaric acid, sodium acetate, pyrothiodecane and tizanidine hydrochloride were added to ethyl acetate and then stirred at room temperature to dissolve them. Then, a solution of the acrylic adhesive polymer in ethyl acetate and the isocyanate crosslinker were added and stirred, and the solution thus obtained was cast on a film of polyethylene terephthalate (PET: 30 μm). The coating was crosslinked thermally at 90° C. for 15 minutes to form an adhesive layer 50 μm thick, and thereafter a patch formulation according to the present invention was prepared.

Example 2

| | |
|---|---|
| Sodium acetate | 9.0% |
| Lactic acid | 2.0% |
| Liquid paraffin | 14.0% |
| Rosin adhesive | 29.0% |
| (KE-311: Arakawa Chemical Industries) | |
| PIB | 13.0% |
| SIS | 18.0% |
| Oxybutynin hydrochloride | 15.0% |
| Total | 100.0% |

From among these, the components except sodium acetate, lactic acid and oxybutynin hydrochloride were dissolved and mixed in toluene. Then, the remaining components were added and dispersed until the mixture became homogeneous, and it was then cast on a film of PET (30 μm) so as to form an adhesive layer 50 μm thick. Thereafter, a patch formulation according to the present invention was prepared.

Example 3

| | |
|---|---|
| Sodium acetate | 9.0% |
| Citric acid | 2.5% |
| Liquid paraffin | 10.5% |
| Polyterpene tackifying resin | 32.0% |
| (ARKON P-100: Arakawa Chemical Industries) | |
| PIB | 13.0% |
| SIS | 18.0% |
| Oxybutynin hydrochloride | 15.0% |
| Total | 100.0% |

From among these, the components except sodium acetate, citric acid and oxybutynin hydrochloride were dissolved and mixed in toluene. Then, the remaining components were added and dispersed until the mixture became homogeneous, and it was then cast on a film of PET (30 μm) so as to form an adhesive layer 50 μm thick. Thereafter, a patch formulation according to the present invention was prepared.

Example 4

| | |
|---|---|
| Sodium acetate | 1.0% |
| Malic acid | 0.3% |
| Liquid paraffin | 27.4% |
| Rosin adhesive (KE-311: Arakawa Chemical Industries) | 27.5% |
| PIB | 12.0% |
| SIS | 22.3% |
| Pyrothiodecane | 3.0% |
| Crotamiton | 5.0% |
| BHT | 0.5% |
| Tizanidine hydrochloride | 1.0% |
| Total | 100.0% |

From among these, the components except sodium acetate, malic acid and tizanidine hydrochloride were dissolved and mixed in cyclohexane. Then, the remaining components were added and dispersed until the mixture became homogeneous, and it was then cast on a film of PET (30 μm) so as to form an adhesive layer 50 μm thick. Thereafter, a patch formulation according to the present invention was prepared.

Example 5

| | |
|---|---|
| Sodium acetate | 1.0% |
| Benzoic acid | 0.3% |
| Liquid paraffin | 27.4% |
| Rosin adhesive (KE-311: Arakawa Chemical Industries) | 27.5% |
| PIB | 12.0% |
| SIS | 22.3% |
| Pyrothiodecane | 3.0% |
| Crotamiton | 5.0% |
| BHT | 0.5% |
| Tizanidine hydrochloride | 1.0% |
| Total | 100.0% |

From among these, the components except sodium acetate, benzoic acid and tizanidine hydrochloride were dissolved and mixed in cyclohexane. Then, the remaining components were added and dispersed until the mixture became homogeneous, and it was then cast on a film of PET (30 μm) so as to form an adhesive layer 50 μm thick. Thereafter, a patch formulation according to the present invention was prepared.

Example 6

| | |
|---|---|
| Sodium acetate | 1.0% |
| Salicylic acid | 0.3% |
| Liquid paraffin | 27.4% |
| Rosin adhesive (KE-311: Arakawa Chemical Industries) | 27.5% |
| PIB | 12.0% |
| SIS | 22.3% |
| Pyrothiodecane | 3.0% |
| Crotamiton | 5.0% |
| BHT | 0.5% |
| Tizanidine hydrochloride | 1.0% |
| Total | 100.0% |

From among these, the components except sodium acetate, salicylic acid and tizanidine hydrochloride were dissolved and mixed in cyclohexane. Then, the remaining components were added and dispersed until the mixture became homogeneous, and it was then cast on a film of PET (30 μm) so as to form an adhesive layer 50 μm thick. Thereafter, a patch formulation according to the present invention was prepared.

Comparative Examples 1 to 6

Comparative Examples 1 to 6 correspond to Examples 1 to 6, respectively, and these procedures followed those of Examples 1 to 6, respectively, except for no addition of sodium acetate used in Examples 1 to 6, to prepare a patch formulation according to the present invention.

Comparative Examples 7 to 9

Comparative Examples 7 to 9 correspond to Examples 1 to 3, respectively, and these procedures followed those of Examples 1 to 3, respectively, except for no addition of the respective organic acids used in Examples 1 to 3, to prepare a patch formulation according to the present invention.

Comparative Example 10

Comparative Example 10 corresponds to Example 4, and this procedure followed that of Example 4, except for no addition of the organic acid used in Example 4, to prepare a patch formulation according to the present invention.

Test Example 1

In Vitro Testing of Percutaneous Absorption

Portions of the dorsal skin were excised in hairless mice (aged from 6 to 9 weeks). After each portion was carefully removed of fat on the dermal side, it was set in the flow-through cell so that the dermal side could contact the receptor phase. Further, in the flow-through cell, water kept at 37° C. was circulated outside of the receptor phase. Each patch (with an area of 5 cm$^2$ where the drug formulation was applied) that was prepared in Examples 1 to 6 and comparative Examples 1 to 10 was attached onto the corneal layer of each portion of isolated dorsal skin, and then the receptor phase, i.e., physiological saline was flown at the rate of approximately 5 ml per hour. A small fraction of the saline was sampled every 2 hours until 24 hours passed after the start, while the flow rate of the receptor phase was precisely monitored. Thereafter, each sample from the receptor phase was analyzed with respect to drug concentration by high performance liquid chromatography in order to calculate cumulative skin permeation, Q, of the drug according to the following equation.

Accumulated skin permeation [Q] (μg/cm$^2$)=[drug concentration (μg/ml)×flow (ml)]/applied area of the drug formulation (cm$^2$)

Flux of skin permeation is defined as a change in the permeation per unit time, and expressed using time, t, as follows:

flux (μg/cm$^2$/hr)=ΔQ (μg/cm$^2$)/Δt (hr)

The greater the value of flux for a formulation, the better percutaneous absorption therefrom. The results are shown in Table 1.

Test Example 2

Testing of Formulation Stability

Each patch for external use that was prepared in Examples 1 to 6 and Comparative Examples 1 to 10 was stored at 25° C.

for 3 months, and then directly observed to see if crystallization had occurred or not therein. In case crystallization occurs with the lapse of time, the appearance of the patch changes which is the checkpoint of its quality, and thus it is not rated stable as a pharmaceutical formulation. Furthermore, crystallization alters the release characteristic and the adhesive property of the formulation, which reasons further that it is unstable. The results are also shown in Table 1.

Overall Evaluation of Percutaneous Absorption and Formulation Stability

With respect to Examples 1 to 6 and Comparative Examples 1 to 10, an example where both percutaneous absorption and formulation stability were rated good was marked with an open circle, although an example where only one or neither of these properties was good was marked with a cross, based on the results of the above Test Examples 1 and 2. The results are also shown in Table 1.

TABLE 1

|  |  | Percutaneous absorption (flux of skin permeation) ($\mu g/cm^2/hr$) | Physical stability of formulation (crystallizability) | Overall evaluation of percutaneous absorption and formulation stability |
|---|---|---|---|---|
| Example | 1 | 3.8 | No crystallization | ○ |
|  | 2 | 23.0 | No crystallization | ○ |
|  | 3 | 27.0 | No crystallization | ○ |
|  | 4 | 4.7 | No crystallization | ○ |
|  | 5 | 5.4 | No crystallization | ○ |
|  | 6 | 4.0 | No crystallization | ○ |
| Comparative Example | 1 | 0.2 | No crystallization | X |
|  | 2 | 1.0 | No crystallization | X |
|  | 3 | 0.9 | No crystallization | X |
|  | 4 | 0.2 | No crystallization | X |
|  | 5 | 0.2 | No crystallization | X |
|  | 6 | 0.1 | No crystallization | X |
|  | 7 | 3.2 | Crystallization | X |

TABLE 1-continued

|  | Percutaneous absorption (flux of skin permeation) ($\mu g/cm^2/hr$) | Physical stability of formulation (crystallizability) | Overall evaluation of percutaneous absorption and formulation stability |
|---|---|---|---|
| 8 | 19.1 | Crystallization | X |
| 9 | 22.1 | Crystallization | X |
| 10 | 3.8 | Crystallization | X |

As evident from the results shown in Table 1, the patches for external use of Examples 1 to 6 where a basic drug, an organic acid and an organic acid salt were combined were good in both percutaneous absorption and stability. On the contrary, the patches for external use of Comparative Examples 1 to 6 where only a basic drug and an organic acid were combined were good in stability but very low in percutaneous absorption. Further, the patches for external use from comparative Examples 7 to 10 where only a basic drug and an organic acid salt were combined were good in percutaneous absorption but very poor in stability.

Industrial Applicability

The present invention provides a patch formulation comprising a basic drug, and having a good percutaneous absorption property of the drug therein and good stability.

The invention claimed is:

1. A matrix patch formulation containing no water for external use, comprising, as essential components:
    1 to 15% by weight of oxybutynine hydrochloride,
    0.3 to 2.5% by weight of citric acid; and
    1.0 to 9.0% by weight of sodium acetate.
2. The matrix patch formulation for external use according to claim 1, wherein the ratio of citric acid to sodium acetate is 1:1 to 1:10 (by equivalent ratio).
3. The matrix patch formulation for external use according to claim 1, wherein the ratio of oxybutynine hydrochloride to sodium acetate is 5:1 to 1:5 (by equivalent ratio).

* * * * *